United States Patent
Deas

[11] Patent Number: 6,010,488
[45] Date of Patent: Jan. 4, 2000

[54] LOWER EYELID RETRACTOR AND METHOD FOR APPLYING MEDICATION TO THE EYE

[76] Inventor: Gerald W. Deas, 109-07 197th St., Queens, N.Y. 11412

[21] Appl. No.: 09/163,030

[22] Filed: Sep. 28, 1998

[51] Int. Cl.[7] .......................... A61M 35/00; A61B 17/02
[52] U.S. Cl. .......................... 604/295; 604/294; 600/236
[58] Field of Search .................................. 600/201, 210, 600/235, 236; 604/294, 295, 300, 302

[56] References Cited

U.S. PATENT DOCUMENTS

| | | | |
|---|---|---|---|
| 3,058,466 | 10/1962 | Routsong | 604/302 |
| 3,872,866 | 3/1975 | Lelicoff | 604/302 |
| 3,934,590 | 1/1976 | Campagna et al. . | |
| 4,257,417 | 3/1981 | Gibilisco | 604/302 |
| 4,605,398 | 8/1986 | Herrick | 604/300 |
| 5,366,448 | 11/1994 | Basilice et al. | 604/302 X |
| 5,429,621 | 7/1995 | Stahl | 604/302 X |
| 5,578,019 | 11/1996 | Feldman . | |

*Primary Examiner*—Jeffrey A. Smith
*Attorney, Agent, or Firm*—Darby & Darby

[57] ABSTRACT

An eyelid retractor, in combination with a medication container, is used to administer medication to an eye of a user. The eyelid retractor may be disposable, and includes an upper portion and a lower portion. The upper portion has an opening, such as a circular and/or flanged aperture, in which a nozzle of a medication container is mounted. The lower portion is connected to the upper portion to move a portion of the cheek of the user. The movement of the cheek retracts the lower eyelid of the user from the sclera of the eye to receive the medication from the nozzle. The retraction the lower eyelid from the sclera of the eye using the eyelid retractor improves the ability and accuracy in self-administering eye drops. The retractor poses less danger from pressure and/or protruding elements near the eye, and retracts the eyelid from the sclera to apply eye drops directly to the sclera with one hand.

24 Claims, 3 Drawing Sheets

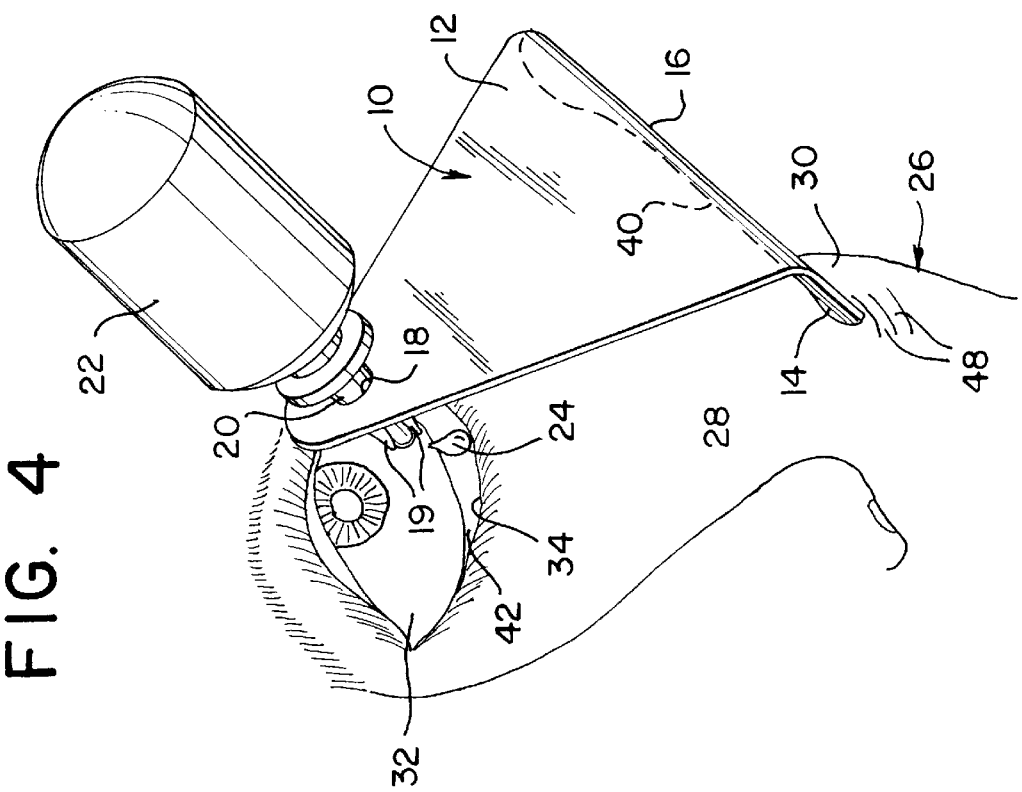
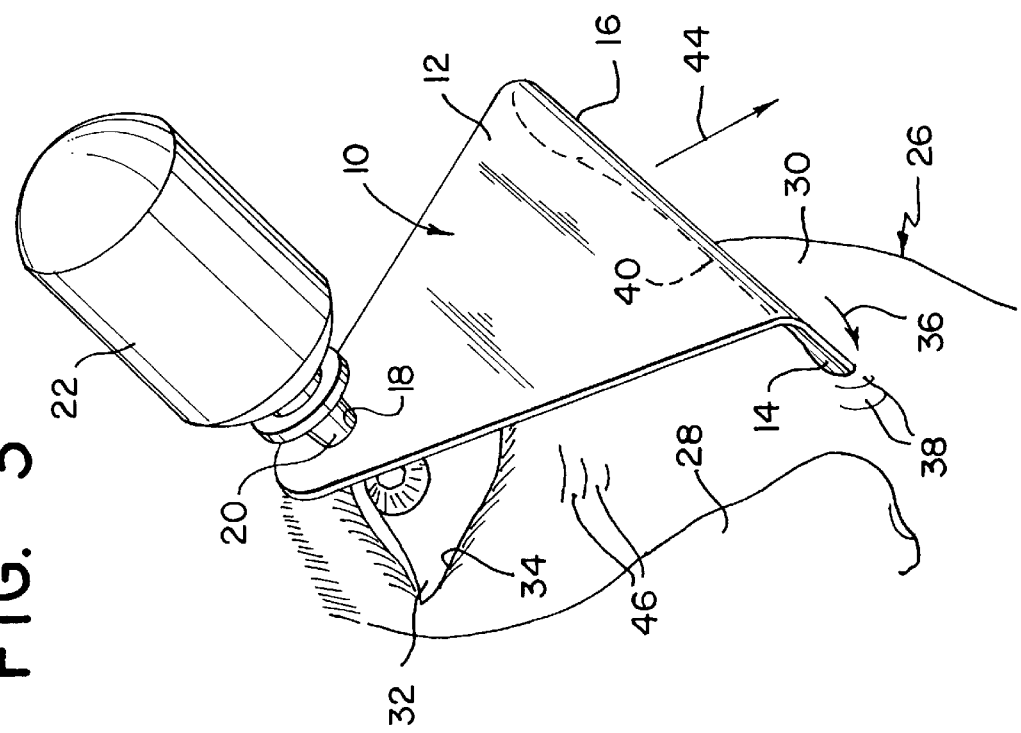

LOWER EYELID RETRACTOR AND METHOD FOR APPLYING MEDICATION TO THE EYE

BACKGROUND OF THE INVENTION

1. Field of the Invention

This disclosure relates generally to the field of medicinal appliers, and in particular to a disposable device and method for the improved self-administration of eye drops.

2. Description of Related Art

The eye consists of living tissues, muscles, and nerves fed by blood vessels. As a result, on occasion, medication needs to be applied to the eye. However, the eye is a quasi-spherical organ, and so the surfaces to which the medication is applied, which are not limited to the fraction of the eye about the iris which is normally visible, are difficult to stabilize during the application of medicine.

When self-administering eye drops, a user typically must retract the lower lid of the eye; for example, to administer the eye drops to the sclera or whitish portion forming the entire eye except for the iris and pupils. Typically, a patient or eye-affliction sufferer may use one's own finger on one hand to retract the eyelid while squeezing medication with the other hand from a dropper containing the eye drop liquid onto the exposed sclera. This traditional approach to instilling eye drops has a number of disadvantages; for example, contact of the fingers with the eyelid and its vicinity, which may promote infections if the fingers are in an unsanitary state.

Also, the process of self-administering eye drops may be inaccurate in that the user has to judge the position and orientation of the eye dropper while both hands are positioned above the face, and are not physically stabilized with respect to each other. Besides wasting medication, inaccurate application of eye drops may reduce the efficacy of the medication, and may also discourage use of eye drops by people who have difficulty in self-administering eye medication.

Other users may be less capable of self-administration of eye drops by the traditional approach. For example, the elderly, arthritis sufferers, and people with poor hand-eye coordination may be inordinately challenged to apply medication to their own eyes. However, in many instances, such users may not have a nurse or home care assistant available to assist or to completely administer such eye drops to such users. Therefore, a need exists for a disposable device or method which improves the ability and accuracy in self-administering eye drops.

In addition, dangers may be encountered from excessive pressures and protruding elements of medicinal applicators used near the eye, such as devices shown, for example, in U.S. Pat. Nos. 3,058,466; 3,872,866; 3,934,590; 4,002,168; 4,085,750; 4,605,398; 5,030,214; 5,064,420; 5,154,710; 5,366,448; 5,429,621; and 5,578,019. Thus, a need exists for a device or method which poses less danger from applying pressure and/or protruding elements near the eye.

Further, the efficacy of the medicinal drops is reduced by applying such drops to the cornea of the eye, as opposed to the sclera under, for example, the lower eyelid. Devices known in the art, such as described in U.S. Pat. Nos. 4,257,417; 5,607,410; and 5,611,788 do not move or retract the lower eyelid, and so apply medication solely to the exposed cornea. In addition, such devices in the prior art may provide excessive pressure in positioning the devices near the eye for applying medication. Thus, a need exists for a device or method which retracts the eyelid from the sclera while preventing excessive pressure from being applied to such regions around the eye.

SUMMARY OF THE INVENTION

The present invention is directed to a disposable retractor and method of use which make it easier to retract the lower eyelid from the sclera of the eye and improve the ability and accuracy of the self-administration of eye drops to the eye, as well as reducing the possibility of infection from use. Such a retractor poses less danger from applying pressure and/or protruding elements near the eye, and retracts the eyelid from the sclera to apply eye drops directly to the sclera while preventing excessive pressure from being applied to such regions around the eye.

In an illustrative embodiment the device for administering medication to an eye of a user includes an upper portion with an opening therethrough. A nozzle of a medication container is mounted to this upper portion and held by, for example, flanges, so the container is on one side and a tip of the dispensing channel of the container is on the other side. A lower portion is connected to the upper portion at an angle so that when the container is positioned above the eye for dispensing medication the lower portion engages the upper cheek or lower eyelid of the user. The device can then be moved so as to retract the lower eyelid of the user from the sclera of the eye to receive the medication from the nozzle.

BRIEF DESCRIPTION OF THE DRAWINGS

The features and advantages of the disclosed lower eyelid retractor and method are readily apparent, and are to be understood by referring to the following detailed description of the preferred embodiments of the present invention, taken in conjunction with the accompanying drawings, in which:

FIG. 3 illustrates a top left side perspective view of the retractor positioned over the eye before retraction of the eyelid;

FIG. 4 illustrates the retractor retracting the lower eyelid for administering medication to the sclera.

DESCRIPTION OF THE PREFERRED EMBODIMENTS

Figure 1:
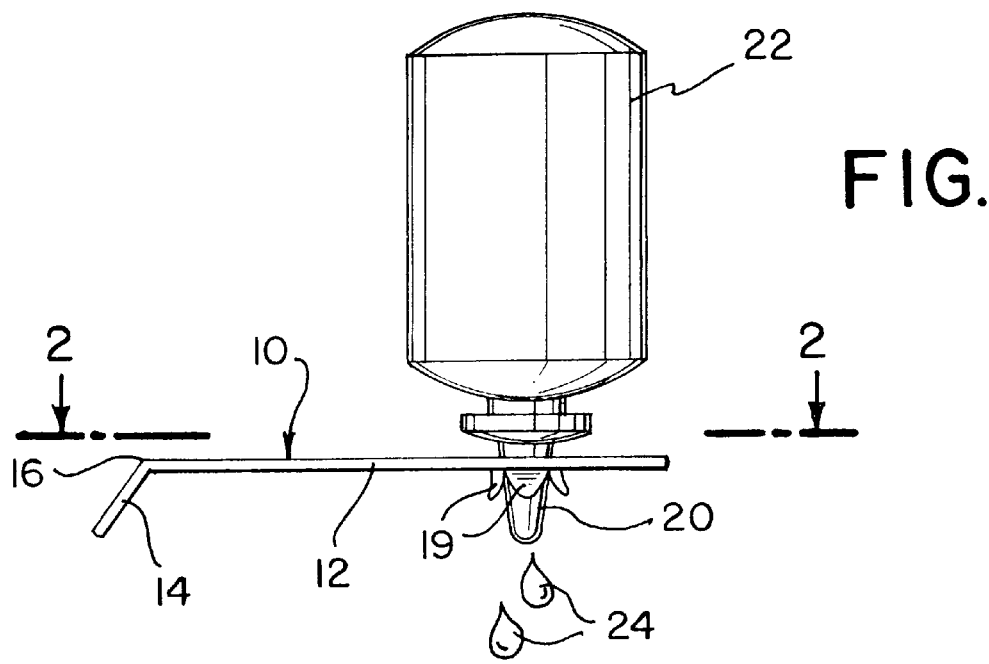
FIG. 1 illustrates a side view of the disclosed retractor with a medication container mounted therein.
Figure 2:
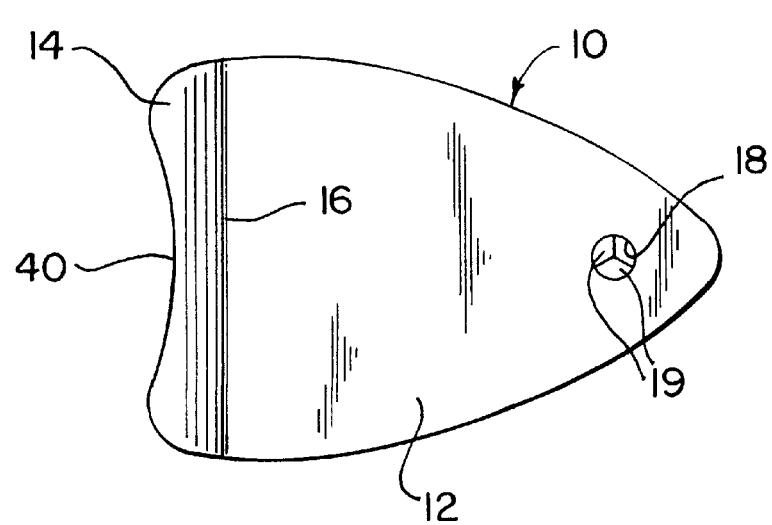
FIG. 2 illustrates a top plan view of the disclosed retractor of FIG. 1 in the direction of arrows 2 with the medication container removed.

Referring in specific detail to the drawings, where common reference numbers identify similar or identical elements, steps, and features, the device and method of the present invention are shown and described. As shown in FIGS. 1 and 2, the device is a lower eyelid retractor 10 and the method of using it enables a person to achieve perfect accuracy when applying eye drops to one's own eyes.

The retractor 10 includes an upper portion 12 and a lower portion 14 connected to the upper portion 12 at a bend 16. In an illustrative embodiment, the portions 12, 14 are substantially planar and the bend 16 forms a predetermined angle between the portions 12, 14. For example, the lower portion 14 may bend away from a plane through the upper portion 12 at an angle of about 45°; or equivalently, the portions 12, 14 may form an angle of about 135°. In a preferred embodiment, the retractor 10 and portions 12, 14 thereof may be composed of a sheet of thin plastic or other relatively rigid materials known in the art, such as polyvinyl chloride (PVC). The retractor 10 and portions 12, 14 thereof may be a one-piece, triangular-shaped unit which may be monolithically formed as a single unit, and may be also be composed of recyclable materials. In addition, the lower eyelid retractor 10 may be sterilized and disposable after, for example, a single use in order to reduce the possibility of infections.

The retractor 10 includes an opening 18 generally located near the apex of the triangle-shaped upper portion 12. The opening 18 may be circular and/or flanged, for example, having flanges 19, and adapted to fit snugly over the nozzle 20 of a medication container such as a bottle 22. The planar upper portion 12 permits a user to hold the bottle 22 without obstruction, such that, typically, squeezing of the bottle 22 causes the eye drops 24 to flow from the nozzle 20.

Due to its triangular shape and planar surfaces, the retractor 10 is adapted to be readily held in one's palm for mounting the nozzle 20 in the opening 18. The nozzle 20 may be force-fitted or friction-fitted into the opening 18 by, for example, the flanges 19, to be removably mounted and so replaceable when the bottle 22 is empty.

Referring to FIGS. 3–4, in using the retractor 10 to assist in self-administering the eye drops 24, the user 26 holds the bottle 22, and then guides the combination of the bottle 22 and the retractor 10 to be positioned on one side of the nose 28 and over the upper cheek 30 or lower eyelid 34 of the user 26, in order to administer the eye drops 24 into the eye 32 above the lower eyelid 34. While the user holds the bottle 22, a slow downward motion of the bottle 22 causes the retractor 10 and the lower portion 14 to move in the direction of the arrow 36, and so to contact the cheek 30 and slightly indent the skin 38. The edges of the retractor 10 may be rounded to gently contact the hands and cheek 30 of the user 26. In particular, the lower portion 14 may have a curved surface 40, as shown in FIGS. 2-3, to contact and rest on the generally curved cheek 30 of the user 26.

Alternatively or in addition to moving the bottle 22 to move the retractor 10 as shown in FIG. 3, the planar upper portion 12 is adapted to receive the palm and/or wrist of the hand of the user 26 which is holding the bottle 22. Accordingly, such downward motion of the lower portion 14 may optionally be caused by corresponding downward motion of the upper portion 12 by the palm or wrist of the user 26.

In a first illustrative use, with the lower portion 14 engaging the cheek 30 as shown in FIG. 3, the retractor 10 is braced adjacent to the face of the user 26 as shown in FIG. 3. Then the retractor 10 with the bottle 22 is gently moved downwardly in the direction of arrow 44 to the position shown in FIG. 4. The effect is to carefully retract the lower eyelid 34 from the sclera 42 of the eye 32, as shown by the straightening of the eye folds 46 of FIG. 3 so they are diminished or do not appear in FIG. 4. The downward motion also causes the lower portion 14 to push the skin 48 of the cheek 30 downward.

Since the hands of the user only contact the retractor 10 and/or the bottle 22 and not the nozzle 20, the retractor 10 promotes more sanitary instillation of the eye drops 24 by eliminating hand-eye contact with the nozzle. In addition, the positioning of the bottle 22 with one's hand and/or the bracing of the retractor 10 in the position shown in FIG. 4 allows the lower eyelid 34 to be held in the retracted position for relatively long periods for applying such mediated drops. Thus, the lowered eyelid 34 is positioned to allow the bottle 22 and nozzle 20 thereof to be held relatively motionless over the center of the eye to accurately instill medicated drops into the eye 32 at a far greater rate than typically performed with traditional eye drop procedures.

The retractor 10 requires little or no coordination or aiming ability, since the retractor 10 holds the nozzle 20 in a fixed position relative to the eye 32 once the lower eyelid 34 is retracted. Accordingly, the retractor 10 reduces the incidences of wasted mediation due to missing the eye 32 from inaccurate aiming.

Figure 5:
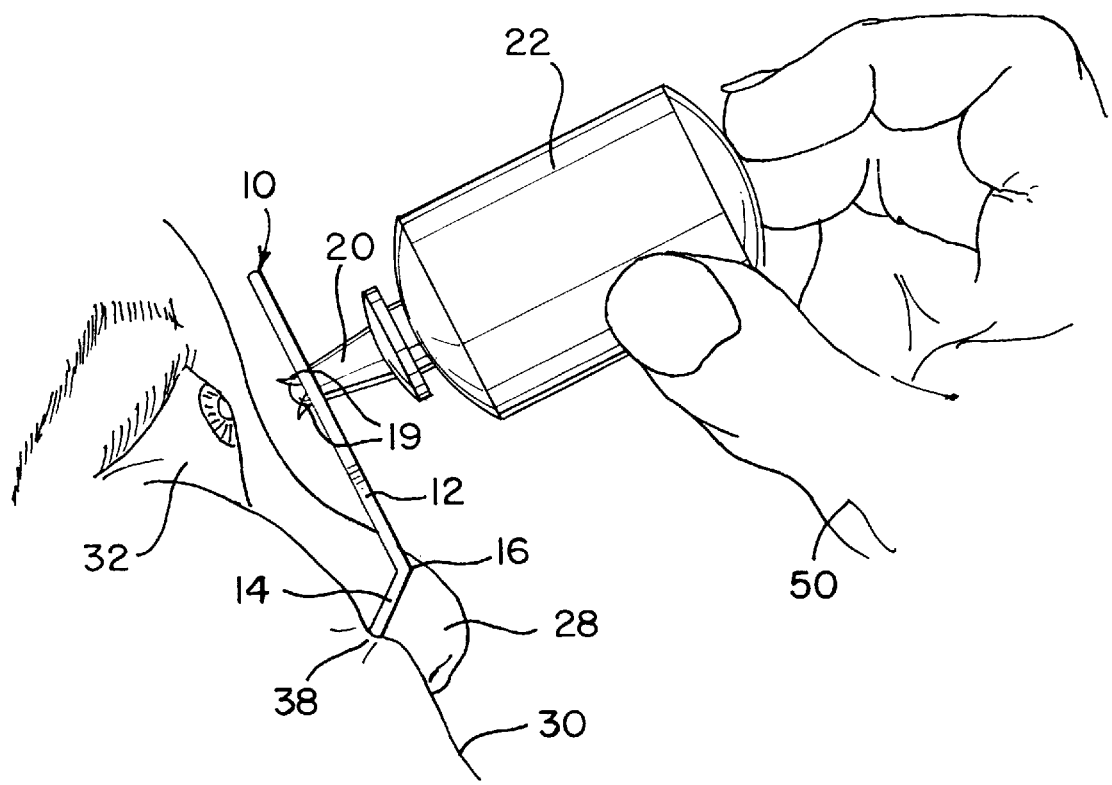
FIG. 5 is a right side perspective view showing the hand of a user applying medication to the sclera using the present invention.

The retractor 10 may be used with one hand 50 of the user as shown in FIG. 5 to apply the medicated eye drops. The one hand 50 has the thumb on one side of the bottle 22, the forefinger on the bottom and the middle finger on the outer side of the bottle. Thus, the one hand 50 can squeeze the bottle and position the retractor to hold the eye open, without requiring another open hand for manually retracting the lower eyelid 34. The use of the retractor 10 for single-handed operation promotes independence among the elderly, arthritis sufferers, and people with poor hand-eye coordination by offering a simple solution to a typically challenging yet routine medication administering procedure.

The disclosed retractor 10 is thus relatively easy to use, as well as easy to fabricate from relatively inexpensive materials. In addition, the safety advantages of a planar upper portion 12 include less danger from protruding elements and the application of excessive pressures near the eye 32. The safety of the retractor 10 is increased by having the pressures used to retract the lower eyelid 34 applied to the cheek 30 at a distance away from the eye 32. Further, due to its relatively simple design, low cost, and case of use, the disclosed retractor 10 may be disposable and/or made of recyclable materials to further increase the sanitary benefits and other advantages in using the retractor 10.

While the disclosed lower eyelid retractor 10 and method of use are particularly shown and described herein with reference to the preferred embodiment, it is to be understood that various modifications in form and detail may be made therein without departing from the scope and spirit of the present invention. Accordingly, modifications such as any examples suggested herein are to be considered within the scope of the present invention, but are not limitations of the invention.

What is claimed is:

1. A device for administering medication to an eye of a user from a nozzle attached to a medication container, the nozzle having a broad base part for attaching the nozzle to the medication container, a dispensing tip for dispensing the medication to the eye and a dispenser portion connecting the base part to the dispensing tip, the dispenser portion being narrower than the base part and having an axis aligned with the dispensing tip, the device comprising:

an upper planar portion forming a major portion of said device, said upper planar portion having an opening extending through it and dimensioned to receive the dispenser portion of the nozzle such that the axis of the dispenser portion is generally perpendicular to said upper planar portion;

means in said opening for frictionally engaging the dispenser portion; and a lower planar portion forming a minor portion of said device, said lower planar portion being connected to said upper portion at an angle thereto and at a position from said opening to allow it to engage a portion of the cheek of the user when the opening is positioned above the eye, so that movement of said device against the cheek and away from the eye causes the retracting of the lower eyelid of the user from the sclera of the eye while the opening is still positioned over the eye.

2. The device of claim 1 wherein said upper and lower portions are angularly oriented at a predetermined bend and said upper portion has a generally triangular shape.

3. The device of claim 1 wherein the upper and lower portions are composed of substantially rigid material.

4. The device of claim 1 wherein the material is a thin plastic.

5. The device of claim 1 wherein the upper and lower portions have rounded edges, particularly the lower portion which engages the cheek.

6. The device of claim 1 wherein said means in said opening is in the form of flanges that are bendable to accommodate dispenser portions of different sizes.

7. The device of claim 1 wherein the device is disposable.

8. The device of claim 1 further including the medication container with the nozzle, said nozzle being mounted in the opening in said upper portion so that upon retraction of the lower eyelid, the nozzle is positioned to deliver medication to the sclera of the eye.

9. The device of claim 8 wherein a length of the dispenser portion of the nozzle is inwardly tapered in a direction from the base part to the dispensing tip.

10. The device of claim 1 further including the medication container with the nozzle mounted in the opening, wherein the nozzle is removably mounted in the opening in the upper portion.

11. The device of claim 1 wherein the opening is spaced at a predetermined distance from the junction of the upper and lower portions such that the nozzle is substantially adjacent to the retracted eyelid for directly administering the medication to the sclera.

12. The device of claim 1 wherein the means in said opening for frictionally engaging the dispenser portion comprises at least one resilient flange directed inwardly from a perimeter of the opening.

13. An eyelid retractor for retracting the lower eyelid to facilitate application of medication to the eye of a user from a nozzle attached to a medication container, the nozzle having a broad base part for attaching the nozzle to the medication container, a dispensing tip for dispensing the medication to the eye and a dispenser portion connecting the base part to the dispensing tip, the dispenser portion being narrower than the base part and having an axis aligned with the dispensing tip, the retractor comprising:

a substantially planar upper portion forming a major portion of said retractor, said upper planar portion having an opening extending through it and dimensioned to receive the dispenser portion of the nozzle such that the axis of the dispenser portion is generally perpendicular to said upper planar portion;

means in said opening for frictionally engaging the dispenser portion; and a lower portion connected at an angle to the upper portion and at a position for contacting a portion of the cheek of the user, whereby movement of the lower portion moves the portion of the cheek when the dispensing tip is above the eye, said lower portion being connected to said upper portion at a position so that movement of the cheek causes retraction of the lower eyelid of the user from the sclera of the eye and the location of the opening over the eye.

14. The eyelid retractor of claim 13 wherein the upper and lower portions form an angle of about 135° at a bend connecting the upper and lower portions.

15. The eyelid retractor of claim 13 wherein said upper and lower portions are composed of substantially rigid material and the upper portion has a generally triangular shape.

16. The eyelid retractor of claim 15 wherein the material is a thin plastic.

17. The eyelid retractor of claim 13 wherein the upper and lower portions have rounded edges at least where the retractor contacts the cheek or hand of the user.

18. The eyelid retractor of claim 13 further including the medication container with the nozzle and wherein the nozzle is removably mounted in the opening in the upper portion.

19. The eyelid retractor of claim 13 wherein the opening is spaced at a predetermined distance from the junction of the upper and lower portions such that the nozzle is substantially adjacent to the retracted eyelid for directly administering the medication to the sclera.

20. The eyelid retractor of claim 13 wherein the retractor is disposable.

21. A method for applying a medication to the eye of a user from a nozzle attached to a medication container, the nozzle having a broad base part for attaching the nozzle to the medication container, a dispensing tip for dispensing the medication to the eye and a dispenser portion connecting the base part to the dispensing tip, the dispenser portion being narrower than the base part, the method comprising the steps of:

providing a retractor with:

an upper planar portion forming a major portion of said retractor having an opening dimensioned to receive the dispenser portion of the nozzle such that the axis of the dispenser portion is generally perpendicular to said upper planar portion;

means in said opening for frictionally engaging the dispenser portion; and a lower portion joined at an angle to said upper portion;

mounting the dispenser portion of the nozzle in said opening such that the axis of the dispenser portion is generally perpendicular to said upper planar portion;

positioning the retractor adjacent to the eye and its corresponding cheek;

moving the retractor in a first direction to cause the lower portion thereof to contact a portion of the cheek;

moving the retractor in a second direction to cause the lower portion to move the portion of the cheek away from the eye, thereby retracting the lower eyelid of the eye of the user from the sclera of the eye; and squeezing the medication container to emit medication through the nozzle and into the eye.

22. The method of claim 21 wherein the step of providing includes the step of:

removably mounting the nozzle in the opening in the retractor.

23. The method of claim 21 wherein the step of providing includes the step of:

providing the opening spaced at a predetermined distance from the lower portion; and wherein the step of moving the retractor in the second direction positions the nozzle to be substantially adjacent to the retracted eyelid for directly administering the medication to the sclera.

24. The method of claim 21 wherein the step of moving the retractor in the second direction includes the step of:

moving the medication container in the second direction, thereby moving the retractor in the second direction.

* * * * *